(12) United States Patent
Perry et al.

(10) Patent No.: US 11,705,240 B2
(45) Date of Patent: Jul. 18, 2023

(54) RESPONSE TO EMERGENCY DEPARTMENT SURGE PREDICTION

(71) Applicant: TeleTracking Technologies, Inc., Pittsburgh, PA (US)

(72) Inventors: Thomas Perry, DuBois, PA (US); Joseph Christopher Schuck, McMurray, PA (US)

(73) Assignee: TELETRACKING TECHNOLOGIES, INC., Pittsburgh, PA (US)

( * ) Notice: Subject to any disclaimer, the term of this patent is extended or adjusted under 35 U.S.C. 154(b) by 176 days.

(21) Appl. No.: 15/859,538

(22) Filed: Dec. 31, 2017

(65) Prior Publication Data
US 2019/0206549 A1    Jul. 4, 2019

(51) Int. Cl.
*G16H 40/20* (2018.01)
*G06Q 10/0631* (2023.01)
*G16H 40/40* (2018.01)

(52) U.S. Cl.
CPC ....... *G16H 40/20* (2018.01); *G06Q 10/06311* (2013.01); *G16H 40/40* (2018.01)

(58) Field of Classification Search
CPC ......... G16H 40/20; G06F 19/30; G06F 19/32; G06F 19/3418; G06Q 50/22; G06Q 50/24
See application file for complete search history.

(56) References Cited

U.S. PATENT DOCUMENTS

| | | | | |
|---|---|---|---|---|
| 7,765,108 B2* | 7/2010 | Goodall | ........... | G06Q 50/22 705/2 |
| 8,073,731 B1* | 12/2011 | Rajasenan | .......... | G06Q 10/0637 705/7.42 |
| 8,515,777 B1* | 8/2013 | Rajasenan | ............ | G06Q 50/22 705/2 |
| 2006/0053035 A1* | 3/2006 | Eisenberg | ............. | G16H 40/20 705/2 |
| 2006/0143060 A1* | 6/2006 | Conry | .................... | G06Q 10/06 705/7.19 |
| 2006/0287906 A1* | 12/2006 | McGillin | ............ | G06F 19/3481 705/2 |

(Continued)

FOREIGN PATENT DOCUMENTS

WO   WO-2013149316 A1 * 10/2013   ....... G06Q 10/06311

OTHER PUBLICATIONS

Steven J. Littig and Mark W. Isken; "Short Term Hospital Occupancy Prediction;" Nov. 28, 2006; Health Care Manage Science; vol. 10; pp. 47-66. (Year: 2006).*

(Continued)

*Primary Examiner* — Jonathon A. Szumny
(74) *Attorney, Agent, or Firm* — Ference & Associates LLC

(57) ABSTRACT

One embodiment provides a method, including: receiving, from a healthcare enterprise system, a notification indicating a need for at least one medical resource during a predetermined time frame at a predetermined facility within the healthcare enterprise system; determining that the indicated need is unavailable during at least one of: the predetermined time frame and the predetermined facility; identifying, based upon the indicated need being unavailable, at least one action to be performed to supply the at least one medical resource; and performing the at least one action. Other aspects are described and claimed.

20 Claims, 3 Drawing Sheets

(56) References Cited

U.S. PATENT DOCUMENTS

| | | | | |
|---|---|---|---|---|
| 2007/0239484 | A1* | 10/2007 | Arond | G06Q 10/0637 705/2 |
| 2007/0282476 | A1* | 12/2007 | Song | G06Q 10/06 700/100 |
| 2008/0109255 | A1* | 5/2008 | Allen | G06Q 10/10 705/2 |
| 2009/0313046 | A1* | 12/2009 | Badgett | G06Q 10/06 705/3 |
| 2010/0198609 | A1* | 8/2010 | Mellin | G06Q 10/06 705/2 |
| 2011/0054946 | A1* | 3/2011 | Coulter | G06Q 10/06 705/3 |
| 2011/0125539 | A1* | 5/2011 | Bollapragada | G06Q 10/043 705/7.12 |
| 2011/0301965 | A1* | 12/2011 | Hitney | G16H 50/20 705/2 |
| 2012/0136671 | A1* | 5/2012 | Alt | G06Q 10/06 705/2 |
| 2013/0204633 | A1* | 8/2013 | Jourdan | G06Q 10/06311 705/2 |
| 2014/0081659 | A1* | 3/2014 | Nawana | G16Z 99/00 705/3 |
| 2014/0288941 | A1* | 9/2014 | Roady | G06Q 50/22 705/2 |
| 2015/0213206 | A1* | 7/2015 | Amarasingham | G16H 50/50 705/2 |
| 2015/0213222 | A1* | 7/2015 | Amarasingham | G16H 50/30 705/2 |
| 2015/0269355 | A1* | 9/2015 | Tidor | G16H 10/20 705/3 |
| 2016/0063196 | A1* | 3/2016 | Dube | G06Q 10/06 705/2 |
| 2017/0024523 | A1* | 1/2017 | Gutfraind | G06N 5/04 |
| 2017/0149701 | A1* | 5/2017 | Mancine | H04L 51/04 |
| 2017/0161614 | A1* | 6/2017 | Mehta | G06N 20/00 |
| 2017/0185721 | A1* | 6/2017 | Schuck | G06F 3/0481 |
| 2017/0372022 | A1* | 12/2017 | Cuellar | G16H 40/20 |
| 2018/0039735 | A1* | 2/2018 | Zhen | G16H 10/60 |
| 2018/0052959 | A1* | 2/2018 | Sharifi Sedeh | G06Q 50/22 |
| 2018/0068078 | A1* | 3/2018 | Barth | G06N 20/00 |
| 2019/0013095 | A1* | 1/2019 | Lawrie | G06Q 50/22 |
| 2019/0035502 | A1* | 1/2019 | Roberts | G16H 40/20 |
| 2019/0174289 | A1* | 6/2019 | Martin | H04W 4/90 |
| 2019/0180868 | A1* | 6/2019 | Makram | G16H 40/20 |
| 2019/0198162 | A1* | 6/2019 | Nunez | G16H 40/20 |
| 2019/0244707 | A1* | 8/2019 | Becker | G16H 40/40 |
| 2019/0304596 | A1* | 10/2019 | Padala | G06Q 10/06375 |

OTHER PUBLICATIONS

Pervaiz et al., "FluBreaks: Early Epidemic Detection from Google Flu Trends," J Med Internet Res. Sep.-Oct. 2012; 14(5): e125. (Year: 2012).*

Dugas et al., "Google Flu Trends: Correlation With Emergency Department Influenza Rates and Crowding Metrics," Influenza Surveillance and ED Crowding, CID 2012:54 (Feb. 15, 2012).*

Davis et al., "Hospital Bed Surge Capacity in the Event of a Mass-Casualty Incident," Prehospital and Disaster Medicine http://pdm.medicine.wisc.edu vol. 20,No. 3 (Year: 2005).*

Dugas et al., "Influenza Forecasting with Google Flu Trends," PLOS ONE | www.plosone.org Feb. 1, 2013 | vol. 8 | Issue 2 | e56176 (Year: 2013).*

Littig et al., "Short term hospital occupancy prediction," Health Care Manage Sci (2007) 10:47-66 (Year: 2007).*

Bonnett et al., "Surge capacity: a proposed conceptual framework," American Journal of Emergency Medicine (2007) 25, 297-306 (Year: 2007).*

Liu et al., "Using Baidu Search Index to Predict Dengue Outbreak in China," Scientific Reports | 6:38040 (Year: 2016).*

Callcut et al., "Finding the signal in the noise: Could social media be utilized for early hospital notification of multiple casualty events?," PLoS ONE 12(10): e0186118. https://doi.org/ 10.1371/journal.pone.0186118 (Year: 2017).*

Fernandez-Luque et al., "Health and Social Media: Perfect Storm of Information," Healthc Inform Res. Apr. 2015;21(2):67-73. http://dx.doi.org/10.4258/hir.2015.21.2.67 pISSN 2093-3681•eISSN 2093-369X (Year: 2015).*

Charles W. Schmidt, "Trending Now Using Social Media to Predict and Track Disease Outbreaks," Environmental Health Perspectives • vol. 120 | No. 1 | Jan. 2012, pp. A31-A33. (Year: 2012).*

Justine Brown, "Using Social Media Data to Identify Outbreaks and Control Disease," https://www.govtech.com/recovery/social-media-data-identify-outbreaks.html. (Year: 2015).*

* cited by examiner

RESPONSE TO EMERGENCY DEPARTMENT SURGE PREDICTION

BACKGROUND

An emergency department (ED) of a medical facility may become a very busy place. The ED often serves as a first stop for patients seeking medical care. These patients may have medical care needs ranging from less serious to life threatening. To serve patient needs, EDs must be staffed and equipped in a manner corresponding to those patient needs. Additionally, the number of patients that present at an ED may provide an indication of patients that will need downstream medical services, for example, in-patient admittance, diagnostic testing, and the like. Accordingly, hospitals try to predict the volume of patients that may present at an ED in order to create staffing schedules, bed assignments, and the like.

BRIEF SUMMARY

In summary, one aspect provides a method comprising: receiving, from a healthcare enterprise system, a notification indicating a need for at least one medical resource during a predetermined time frame at a predetermined facility within the healthcare enterprise system; determining that the indicated need is unavailable during at least one of: the predetermined time frame and the predetermined facility; identifying, based upon the indicated need being unavailable, at least one action to be performed to supply the at least one medical resource; and performing the at least one action.

Another aspect provides an information handling device, comprising: a processor; at least one sensor operatively coupled to the processor; a memory device that stores instructions executable by the processor to: receive, from a healthcare enterprise system, a notification indicating a need for at least one medical resource during a predetermined time frame at a predetermined facility within the healthcare enterprise system; determine that the indicated need is unavailable during at least one of: the predetermined time frame and the predetermined facility; identify, based upon the indicated need being unavailable, at least one action to be performed to supply the at least one medical resource; and perform the at least one action.

A further aspect provides a product, comprising: a storage device that stores code, the code being executable by a processor and comprising: code that receives, from a healthcare enterprise system, a notification indicating a need for at least one medical resource during a predetermined time frame at a predetermined facility within the healthcare enterprise system; code that determines that the indicated need is unavailable during at least one of: the predetermined time frame and the predetermined facility; code that identifies, based upon the indicated need being unavailable, at least one action to be performed to supply the at least one medical resource; and code that performs the at least one action.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
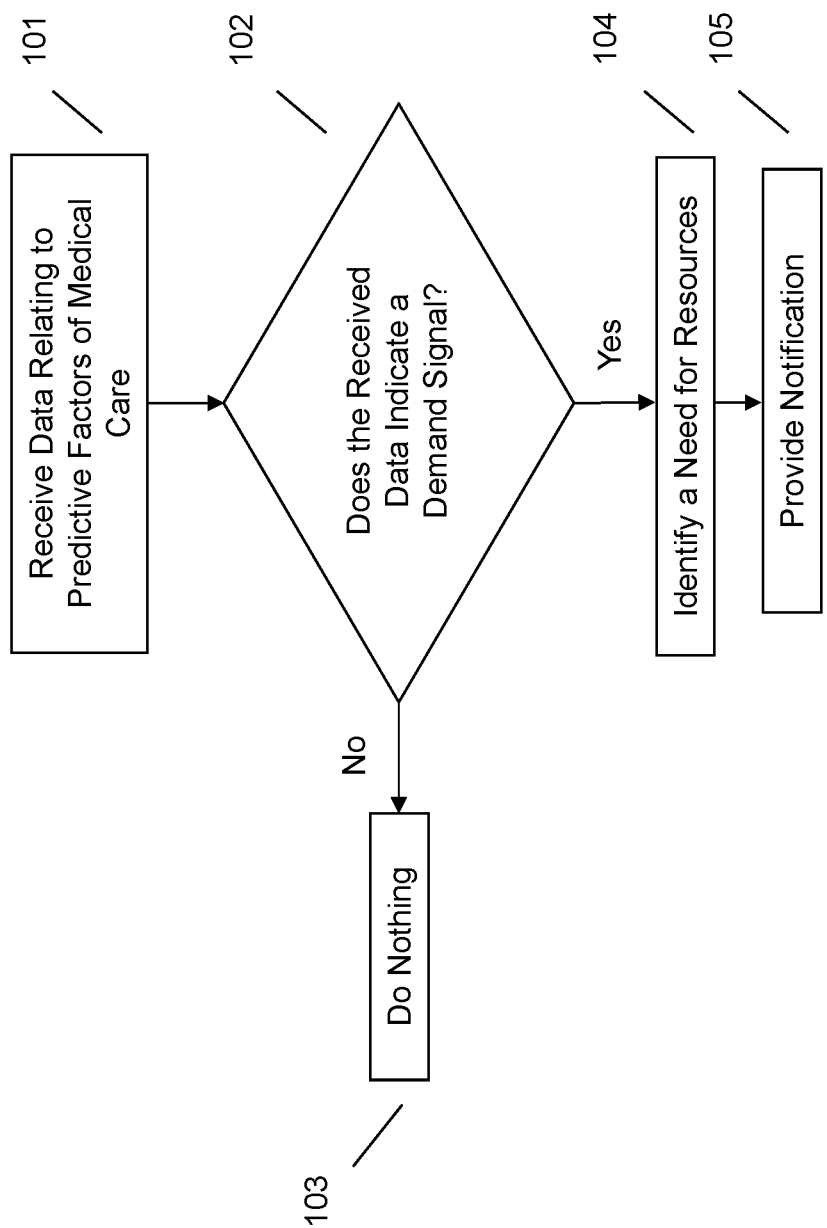
FIG. 1 illustrates an example method of estimating a patient surge based upon received data.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Predicting the volume of patients that will present at an ED may be difficult since patients present with a wide spectrum of symptoms, ailments, and the like, and different environmental conditions may cause an influx of patients that were not expected. For example, weather conditions, large-scale events, or the like, may result in more patients presenting at the ED than a typical day. Over or underestimation of a volume of patients impact both healthcare costs and patient care, for example, because staffing is based upon an estimation of the number of patients that will arrive at the ED in a particular shift. Thus, the more accurate the estimate, the more accurate staffing and resource allocation.

Hospital emergency departments (EDs) may be the first point of contact a presenting patient has with a healthcare system. A patient may be sick, injured, or the like. A patient may arrive at the ED alone, be transported by a companion or ambulance, or by referral from another medical facility. It may be difficult for the ED to predict how many patients will present at the ED in a given time frame. Also, it may be difficult to predict what symptoms or injuries will present at the ED. A better prediction allows an ED to better staff and equip the facility in preparation for patient care. Typical patient loads may be identifiable and easy to identify. However, an ED may experience a surge, or an increase in demand for medical care. For example, an ED may experience a surge in the number of patients presenting if there is a flu outbreak in a geographic region. As another example, a surge of patients may occur from a mass casualty event. For the purposes of this disclosure, casualty includes non-deadly injuries as well. Predicting both the number and severity of symptoms helps an ED and associated hospital departments or facilities to better respond to the surge.

In current systems, surge prediction may be estimated. Such predictions may be based on known medical care trends. For example, during cold and flu season, the ED may have staff ready to respond to these symptoms. As another example, an ED may prepare (e.g., increase staffing, increase resources, better allocate downstream resources, etc.) around times or holidays known to have an increase in motor vehicle accidents. Such predictions remain somewhat crude and rely on past observations of presenting patients. However, if an expected influx of patients is experienced, incoming patients may quickly overwhelm the system. An overstaffed ED adds to healthcare costs, and an understaffed ED does not serve the patient care needs. Current predictions for ED surge do not model many variables that may help to predict an ED surge.

Additionally, current surge prediction does not take into account real-time events that lead to a change in the volume or severity of patient care. For example, if there is a mass casualty event such as a transportation accident, demonstration, natural disaster, terrorist act, or the like, then the ED department may experience a surge. Each event will have a unique number and type of care associated with the mass casualty event. As another example, a geographic region may experience a sudden outbreak in a disease (e.g., flu, pneumonia, virus, etc.) that results in a surge in emergency room visits by patients. Current systems do not integrate this real-time information into the surge prediction. Real-time information about such events in real-time allows an ED to make better staffing choices and predict other needs as they occur, for example, downstream resources that will be necessary for treating patients. The problem with being unable to account for a possible surge is that the hospital may have to divert patients to different facilities, which is undesirable to the hospital. Thus, the hospital, if at all possible, would like to account for the surge. Therefore, if the surge can be predicted the hospital can account for the surge, thereby preventing any possible diversions.

Even if a prediction of a possible surge is made, these predictions may not coordinate the ED with other departments both within the hospital and at other medical facilities. For example, a certain percentage of emergency department patients may be admitted to the in-patient care facility. Thus, if the emergency department experiences a surge, the in-patient care facility will also experience a surge. Thus, knowing there may be a surge in patient influx allows for better resource management for not only the emergency department, but also the larger healthcare system.

A surge of patients impacts many aspects of the ED and other healthcare facilities both within and outside the hospital. For example, if a surge may occur there may be a need to free up beds, or places for incoming patients. As an example, with a surge to the ED, there may be a need to "step down" intensive care unit (ICU) patients that are ready in order to free up ICU space for more serious incoming ED patients. Also, patients ready to be discharged in other care units may be discharged earlier in the day as opposed to waiting to a standard discharge time in order to free up the bed or room for other expected patients. If an ED is at capacity or over capacity with respect to resources, then incoming patients may be diverted to other medical care facilities such as urgent care facilities, clinics, physician offices, lower level trauma centers, or the like, which may result in lower quality care, higher care times, and costs to the hospital.

Accordingly, an embodiment provides a method for identifying a demand signal or surge for an emergency department using at least one information source with a stream of data relating to a set of predictive factors. In an embodiment, the system may notify a user of a need for at least one medical resource in response to the identification of a demand signal. The system may receive, from at least one information source, a stream of data relating to a set of predictive medical care requirements. In an embodiment, an information source may be historical data, news reports, first responders, emergency dispatches, social media, Internet searches, individuals, other healthcare facilities, or the like. In an embodiment, at least a portion of the stream of data may be analyzed for an indication of a demand signal in which an influx of patients may occur. In other words, the stream of data can be analyzed to determine if a surge of patients into an emergency department may occur. Based on the demand signal, the system may identify a need for at least one medical resource. In an embodiment, a notification may be provided of a need for at least one medical resource.

The illustrated example embodiments will be best understood by reference to the figures. The following description is intended only by way of example, and simply illustrates certain example embodiments.

FIG. 1 illustrates a method of predicting a possible emergency department surge based upon data streams that include predictive factors that may indicate the surge. At 101, an embodiment may receive from at least one information source, a stream of data relating to a set of predictive factors of medical care requirements. In an embodiment, an information source may be historical data, news reports, social media, internet searches, first responders, emergency dispatch centers, medical facilities, transportation authorities, individuals, a combination thereof, and the like. For example, the system may receive information about a mass casualty event from a social media feed, an emergency dispatch, news reports, or the like. As another example, the system may receive information from Internet searches from at least one individual searching for symptoms such as a cold, flu, or the like. For example, in a geographic region, the system may identify that an increase in searches for flu symptoms has occurred. In an embodiment, the system may be updated by individuals both within and outside the healthcare system and/or may access third-party sources. The received stream of data may be analyzed as described below.

In an embodiment, the system may receive a stream of information by sensing trends in Internet context. For example, the system may watch for an increase in the discussions or searches, for example, on social media sites, on Internet search engines, or the like, relating to at least one medical condition and symptom (i.e. cold, flu, disease, malady, injury, reports of mass casualty, etc.). In other words, the system may mine social media feeds and identify that a lot of people are discussing illness symptoms and may thus indicate a need for medical care.

In an embodiment, the system may collect information directly from a source upstream of ED medical care. An upstream source may include emergency dispatch centers, first responders, urgent care facilities, other hospitals, physician offices, transportation authorities, patient transport entities, or the like. For example, other medical facilities (e.g., urgent care facilities, primary physicians, etc.) may provide information indicating that these facilities have experienced an influx of patients, which may be indicative of other facilities, such as an emergency department, experiencing an influx of patients.

In an embodiment, the information source is "mined" for information pertaining to a set of predictive factors of medical care requirements. For example, if a patient searches for nasal drip, fever, and a headache, the system may categorize the symptoms as a possible cold. Additionally or alternatively, the system may keep these symptoms as separate symptoms and compare the symptoms to other collected data observing trends across a population. In this manner, an embodiment may collect information about a possible outbreak of a disease much more severe than a common cold. In an embodiment, the collection of information relating to medical information may be received or obtained from emergency dispatch centers, first responders, urgent care facilities, other hospitals, physician offices, transportation authorities, patient transport entities, or the like.

In an embodiment, the system may use a database, historical data, or the like, to interpret a symptom or a plurality of symptoms to determine patterns of predictive factors of medical care requirements. For example, the system may access a database including information related to illnesses and correlate the symptoms with possible illnesses. In order to determine a possible emergency department surge, the system may filter a stream of data based upon a geographic region, demographic data, temporal relationships, or the like, for example, to determine if a particular facility will experience a surge. In an embodiment, the system may collect a volume of information of which all or a subset may be analyzed. Additionally or alternatively, the system may collect a stream of information from dispatch centers such as 911 call centers, first responder communications, transportation authorities, patient transport entities, hospitals, medical facility computer systems, or the like. In an embodiment, the stream of information may comprise electronic data, real-time or prerecorded audio communications, video, photographs, print media, word of mouth, or the like. Other information streams and data are possible and contemplated, for example, any information source that may be related to medical care.

At 102, an embodiment may analyze whether at least a portion of the stream of data indicates a demand signal where the demand signal may include an influx of patients seeking medical care, for example, at an emergency department or other medical facility. In other words, the data is analyzed to determine whether the information indicates that a surge may be imminent or possible. Thus, the stream of data relating to a set of predictive factors of medical care requirements may be analyzed to predict a demand signal. In other words, a demand signal may be an increased or unpredicted increase in the volume of patients presenting at an ED. In an embodiment, the system may analyze data either from local, regional, country-wide, or international communities in healthcare needs to predict a demand signal.

A demand signal may be determined from a stream of information. For example, if there is a multivehicle pile-up on an interstate in the area served by the ED, then a demand signal may be indicated from one or more streams of data, for example, first responders, news reports, dispatch centers, patient transport, eyewitness information, or the like. In an embodiment, the stream of data may comprise information related to the number, severity, type, location, time, and the like, information. For example, in a multiple vehicle pile-up, there may be injuries ranging from less serious cuts or abrasions, bone fractures, or serious head trauma. The system may analyze the severity level of different patients and analyze a stream of information.

While the multiple vehicle pile-up is an illustrative example, the system may be used for any range of patient needs from simple maladies to mass casualty events. In an embodiment, the system may use the volume of possible presenting patients to an ED to determine a surge. Additionally or alternatively, the system may use the severity and/or type of injury and/or symptom to determine if a demand signal exists. In other words, the system may determine a surge in the volume of patients, and may also determine a surge in a type of patient. The type of patient may be indicative of the need for certain types of resources that may not be needed with other types of patients.

In an embodiment, in analyzing the data the system may use natural language processing (NLP) techniques. The NLP techniques may be used by the system to determine syntax of the data stream, terms within the data stream, or the like. For example, the system may search for semantics in a stream of data such as machine translation, named entity recognition, optical character recognition, relationship extraction, sentiment analysis, word sense disambiguation, or the like. This processing may then allow the system to parse the data streams, extract terminology or phrases within the data streams, or the like, which then provides a mechanism for understanding and analyzing the data streams. In an embodiment, the system may search for speech input in a stream of data using speech recognition, speech segmentation, text-to-speech, or the like, and use natural language processing to identify predictive factors and/or a demand signal. In an embodiment, the system may search for discourse information in a stream of data using automatic summarization, co-reference resolution, discourse analysis, and the like. In an embodiment, these NLP techniques may be used in any combination to provide analysis to a system.

If the system determines as 102, that the data does not indicate a demand signal, an embodiment, at 103, then the system may do nothing or take no further action. In an embodiment, the system may determine there is not a demand signal from a stream of data that relates to patient medical care. It should be noted that even if no current demand signal is determined, the information from a data stream may be retained for later use. A later use may include later analysis, compounding the past data with ongoing or future data, using the data for identifying historical data trends in the future, or the like. For example, a stream of data may show only a single or small number of patients that may present to an ED, and a demand signal may not be determined. However, as time passes, more patients with similar symptoms or even different symptoms may be received by the system thereby creating a demand signal. In the future, the system may identify that the small number of patients presenting was indicative of a later surge.

If, at 103, the system determines that the data does indicate a demand signal, the system may analyze the stream of information to identify a need for at least one medical resource at 104. For example, the analysis may include comparing the predicted demand signal to staffing, bed space, and other medical resources, that are currently scheduled or being scheduled for a medical facility, for example, an emergency department. For example, if there are patients with bone fractures, the ED may identify staffing and resources pertinent to that type of care, such as orthopedic physicians, equipment to treat bone fractures, and the like. If the number of patients with bone fractures exceeds the staffing or resources currently available in an ED, a notification or other alert may be provided at 105.

Figure 2:
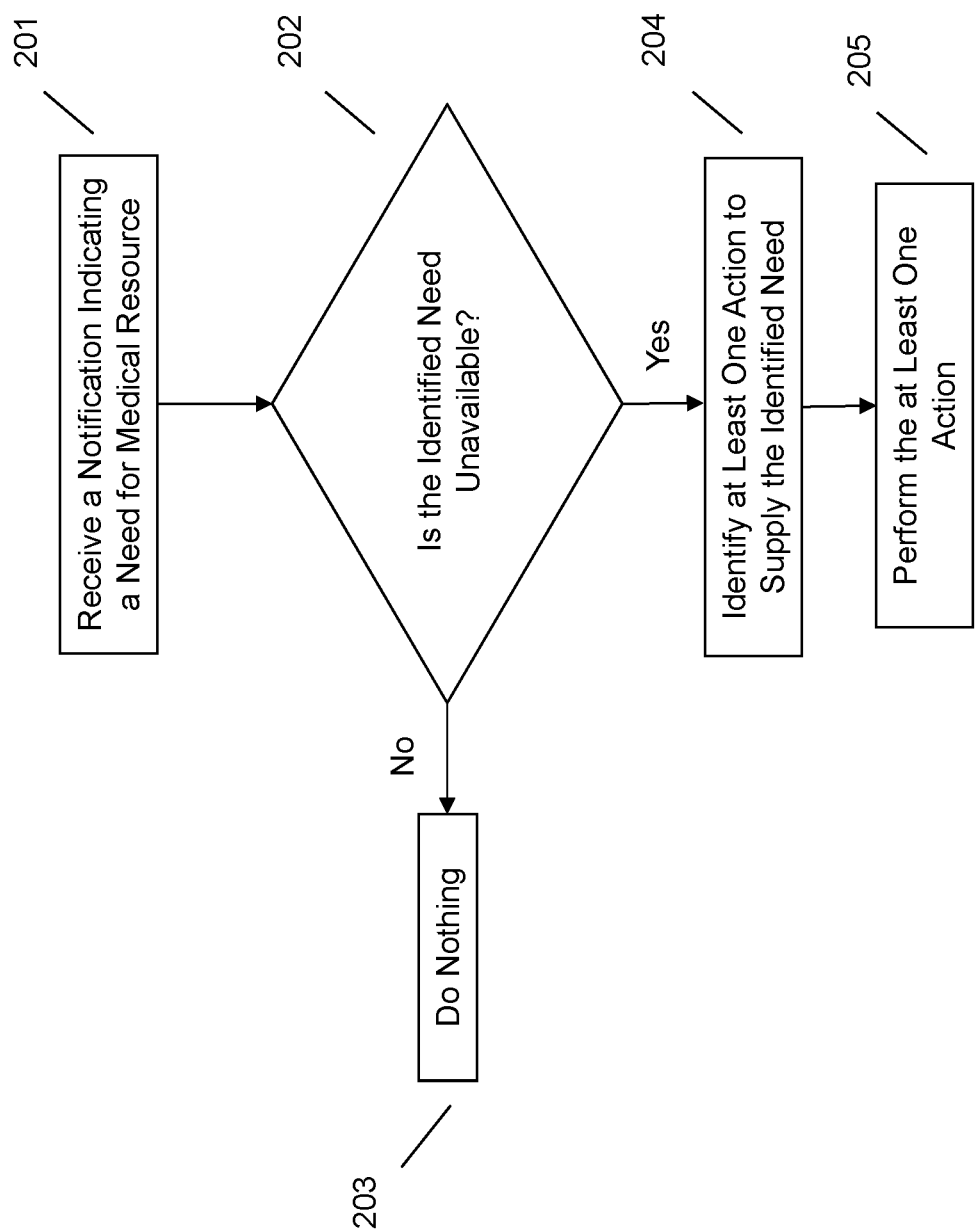
FIG. 2 illustrates an example method of responding to an estimated patient surge.

With reference to FIG. 2, and upon receiving this notification that a need for at least one medical resource exists at 201, the system may determine if the identified need is unavailable at the predetermined time frame and/or predetermined facility at 202. To determine if the identified need is unavailable, the system may compare the predicted surge level with the currently available, or future availability, of the identified at least one medical resource (e.g., staff, medical procedure object (e.g., stethoscope, medicine, blood pressure monitor, etc.), location resource (e.g., bed, room, etc.), etc.). In other words, in an embodiment, the system may check the current capacity of a department and compare this capacity with a predicted surge level. In an embodiment, the system may check scheduling of patient care and/or staff. For example, the system may inquire to the current capacity of the ED using factors such as staff, both present and turning over, bed space, equipment availability, supplies, and the like.

In an embodiment, the system may check staff scheduling. For example, the system may receive a demand signal and check on current staff resources. The system may check scheduling of at least one department and may determine the flow of staff on duty. Additionally, the system may access vacation or requested vacation schedules to determine staffing levels. If the identified need is available, the system may take no further action at 203. Alternatively, the system may put a hold on the identified need so that it is available at the predetermined time and predetermined location. If a demand signal indicates that more staff may be necessary, then the system may alert the healthcare facility. In response to this alert and upon determining that the identified need is unavailable, the system may identify at least one action that could be performed to supply the identified need at 204 and may subsequently perform one or more of the identified actions at 205.

For example, if the identified need is a bed of a facility located downstream, workflow-wise, from the emergency department facility (i.e., a facility that a patient may be moved to upon discharge from the emergency department (e.g., in-patient care, rehabilitation, etc.)), the system may identify at least one bed within the facility that can be made available. As should be understood by one skilled in the art, a healthcare enterprise is intended to describe an entire enterprise under a single healthcare provider. In other words, a healthcare enterprise may include one or more buildings that may be located in one or more buildings in one or more geographical areas. Each of the departments within the healthcare enterprise may be referred to herein as a "facility". For example, the emergency department may be one facility, the long-term care department may be another facility, the in-patient department may be another facility, and the like. Each of the facilities may be located in separate buildings or may be located within the same building. For example, an emergency department may be located within the same building as an in-patient care facility.

In the example referred to the preceding paragraph, the system may identify whether any patients that are currently in the facility could be discharged at a time that occurs prior to the predetermined time frame. This may occur when the patient is scheduled to be discharged, but the typical discharge time is in the late afternoon. The system may then identify that the discharge could be moved to an earlier time. The system may then perform the action of rescheduling the discharge times. The system may also identify that the bed is no longer occupied but it has not been cleaned by environmental services. The system may then perform the action of notifying environmental services that the bed should be cleaned prior to the predetermined time frame.

As another example, if the at least one medical resource that is identified as a need is at least one staff member, the system may access schedules of staff members to determine if the staff could be rescheduled to account for the identified need. The system may also identify if some staff could be extended or called-in to supply the identified need. The system may then perform the action to reschedule the staff, notify on-call staff, notify staff already present that there is a request to remain at the facility, or the like. As a final example, the identified at least one medical resource may include a medical procedure object (e.g., blood pressure monitor, medical cart, wheelchair, stethoscope, medicine, ambulance, etc.). The system may identify a current location of the medical procedure object and determine that it is not at the needed location. Thus, the system may perform the action of providing instructions or a notification to transfer the identified at least one medical procedure object to the predetermined facility before the predetermined time frame.

In an embodiment, a need for at least one medical resource may be within or outside the emergency department. For example, in a multiple vehicle crash, a stream of data may indicate a number of patients with head trauma requiring surgery. The system may identify that surgical suites or operating rooms (OR) should be available when these patients arrive. Accordingly, the system may identify the need for the OR resource and check scheduling of the OR facilities. If the identified medical resource is available, the system may take no further action. If, however, the medical resource is not available, the system may provide a notification at 105, which then may trigger the system to identify actions that can be performed to supply the identified need, for example, as illustrated in FIG. 2. The need for a resource may also trigger an action to compensate for the identified need. For example, if an OR resource is needed and unavailable, the system less time sensitive surgeries, such as elective surgeries, that may be rescheduled to allow the head trauma patients to receive immediate care.

In an embodiment, the system may identify a need for resources such as a bed or patient room. In an embodiment, if a demand signal is determined, then there may be a need for more space in the ED or another area of medical care. For example, if a demand signal is determined from a stream of data, there may not be space for the incoming patients. If there is an influx of newly admitted patients, then there may be a need to discharge patients that are ready for discharge. For example, many hospitals discharge patients at a set time and the set time may be in the early afternoon. If there is a need for beds, a hospital may discharge patients slightly earlier in the day if medical care is complete such that the incoming patients may have a bed.

In an embodiment, the system may identify any number of medical resources. Patient care requires many support functions beyond physicians and nurses. These support functions or "service lines" include technicians, administrative staff, room cleaners, environmental systems, food services, patient transport infrastructure, stocked goods, blood banks, tissue banks, organ donors, urgent care facilities, clinics, ambulance services, information technology, and the like. A need for any one or combination of these resources may be identified by the system in response to a demand signal.

In an embodiment, a need for resources may be identified based on patient symptoms or condition. Medical needs may vary greatly from patient to patient. A stream of information either at the time of admission or from upstream sources (i.e.

first responders, authorities, or the like) may provide information of a probability that a patient may be admitted to the ED. For example, a male patient of around 60 years of age complaining of chest pain has a much greater probability of admission to an ED as compared to a man in his early 20s presenting with cold-like symptoms.

In an embodiment, the system may use factors such as symptoms to assign a probability of admission to the ED. A probability of admission may be used by the system to predict a demand signal. For example, a very high probability may indicate a need for space in the ED. However, a large number of patients presenting to an ED even with a low level of probability of admission to an ED may still indicate a demand signal. Although these lower level probability patients may not be admitted, the patients may still require staff and resources either within the ED or elsewhere in a healthcare system.

At 105, in an embodiment the system may provide a notification of the need for at least one medical resource. In an embodiment the resource may be within an ED. Additionally or alternatively, the notification may be to a site outside the ED. In an embodiment, the notification may serve to help "decompress" the medical facility, for example, by allowing the system to perform actions to supply the identified need, as illustrated in FIG. 2. Decompressing may serve to free up bed space, staff, resources, or the like, which may be within the ED or downstream of the ED. For example, the system may notify staff coordinating patient discharge so that a patient ready to leave the care facility may be discharged earlier.

The notification may alert departments such as intensive care units (ICUs) so that patients ready to "step down" to lower units may be moved to those lower units to make space for incoming patients. The notification may be to environmental services that incoming patients may require those beds, and routine cleaning tasks of, for example common areas, should be put off to a later time to prioritize the room cleanup. The notification may notify on-call staff to come to the facility to meet the demand signal. The notification may be sent to an inventory scheduler to check medical resource (e.g., bandages, tools, medicines, etc.) levels and needs with respect to the possible surge. The notification may be sent to any staff, resource, department, or the like, indicating a possible need for a service in patient care.

In an embodiment, the notification signal may in one or many forms of communication. In an embodiment, a notification may be a system alert, screen alert, email, text message, phone call, page, social media post, on a website, on any device carried or used by healthcare professionals, or the like. The notification recipient list may be customized. For example, all staff, only specific departments, only specific specialties, only those on-site, only those on-call, any combination thereof, or the like, may be notified of the resource need. In an embodiment, the system may alert the general public, government officials, first responders, healthcare supervisors, healthcare staff, healthcare administrators, healthcare support staff, patient transport entities, nursing homes, behavioral healthcare facilities, physician offices, or the like.

The decompressing may relieve the influx of patients to an ED by shunting patients to another facility. If a demand signal occurs, then the system may notify healthcare entities upstream of the ED. For example, if an ED receives a demand signal, the notification may be to an ambulance service to take patients with less severe injuries to a lower level trauma center freeing up resources at a level 1 trauma center for the most severe injuries. Additionally or alternatively, a notification may be sent out to urgent care facilities or other healthcare offices that a demand signal exists and only the most severe patients should be sent to the ED experiencing a demand or surge. In other words, if the expected number of patients exceeds a capacity of the emergency department, some patients that were scheduled to arrive at the emergency department may be routed to a different facility. For example, rather than routing an ambulance to the expected over capacity emergency department, the system may route the ambulance to a different emergency department, thereby creating a more efficient patient care and flow.

In an embodiment, a notification may alert other entities of a health issue affecting the community. For example, the system may detect a large number of patients either searching or presenting with a group of symptoms indicative of an infectious disease. A notification may alert emergency responders, ambulance services, urgent care facilities, medical offices, or the like, of an outbreak of a disease.

In an embodiment, a notification may alert departments that support healthcare. Healthcare facilities may include very complex environmental, electrical, plumbing, food service, machinery, or the like, systems. For example, if a demand signal is provided in conjunction with a natural disaster such as a hurricane or ice storm, there may be an interruption of commercial power to a healthcare facility. The system may notify the department in charge of the healthcare facility's generators that the facility may need to begin to use the alternate power source. As another example, the system may provide a demand signal to food service to meet demands of more patients, staff, and visitors to a healthcare facility. In other words, the system may provide a notification to any department or entity involved in any aspect of a healthcare facility.

Such a system provides a technical improvement to current emergency department surge predictors. Rather than merely using historical information to attempt to predict patient flow, the systems and methods described herein use both historical and real-time information to predict a possible surge. The system then provides notifications to personnel that a surge is expected and to prepare for the same. Thus, the systems and methods as described herein provide a technique that allows for more efficient and effective management of medical resources based upon expected patient loads that are derived from different data sources.

Figure 3:
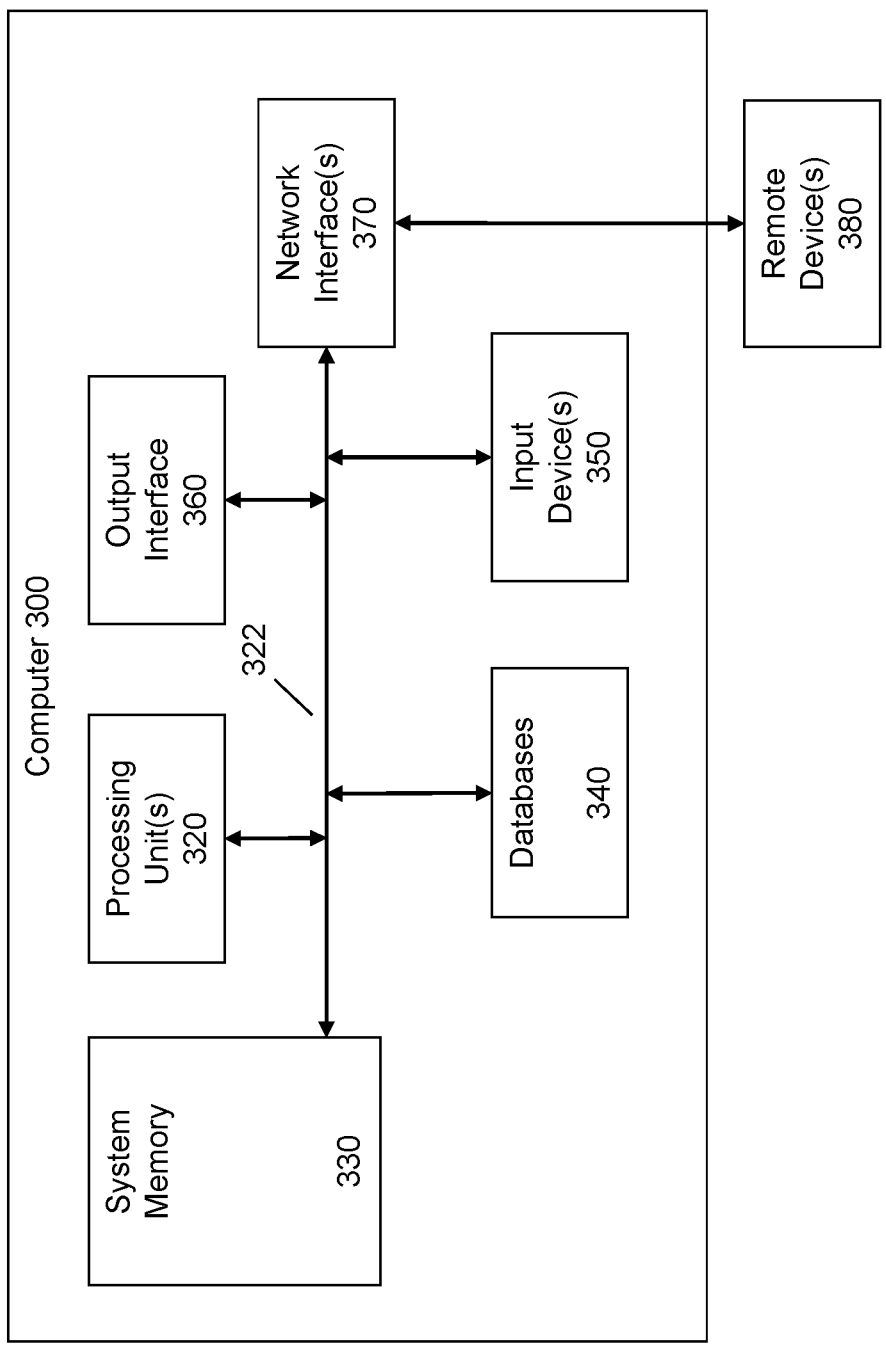
FIG. 3 illustrates an example of device circuitry.

While various other circuits, circuitry or components may be utilized in information handling devices, with a computer, server, client device or the like, an example device that may be used in implementing one or more embodiments includes a computing device in the form of a computer 300 as illustrated in FIG. 3. This example device may be a server used in one of the systems in a hospital network, or one of the remote computers connected to the hospital network. Components of computer 300 may include, but are not limited to, a processing unit 320, a system memory 330, and a system bus 322 that couples various system components including the system memory 230 to the processing unit 320. Computer 300 may include or have access to a variety of computer readable media, including databases. The system memory 330 may include non-signal computer readable storage media, for example in the form of volatile and/or nonvolatile memory such as read only memory (ROM) and/or random access memory (RAM). By way of example, and not limitation, system memory 330 may also include an operating system, application programs, other program modules, and program data.

A user can interface with (for example, enter commands and information) the computer 300 through input devices 350. A monitor or other type of device can also be connected to the system bus 322 via an interface, such as an output interface 360. The computer may include a database 340. In addition to a monitor, computers may also include other peripheral output devices. The computer 300 may operate in a networked or distributed environment using logical connections to one or more other remote device(s) 380 such as other computers. The logical connections may include network interface(s) 370 to a network, such as a local area network (LAN), a wide area network (WAN), and/or a global computer network, but may also include other networks/buses.

Information handling device circuitry, as for example outlined in FIG. 3, may be used in client devices such as a personal desktop computer, a laptop computer, or smaller devices such as a tablet or a smart phone. In the latter cases, i.e., for a tablet computer and a smart phone, the circuitry outlined in FIG. 3 may be adapted to a system on chip type circuitry. The device, irrespective of the circuitry provided, may provide and receive data to/from another device, e.g., a server or system that coordinates with various other systems. As will be appreciated by one having ordinary skill in the art, other circuitry or additional circuitry from that outlined in the example of FIG. 3 may be employed in various electronic devices that are used in whole or in part to implement the systems, methods and products of the various embodiments described herein.

Additionally details regarding the above discussed embodiments can be found in co-pending and commonly assigned U.S. patent application Ser. No. 15/859,537, titled "EMERGENCY DEPARTMENT SURGE PREDICTION" the entirety of which is filed concurrently herewith and incorporated by reference herein.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device that are executed by a processor. A storage device may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method comprising:

receiving, from at least one of a plurality of information sources, a stream of data relating to a set of predictive factors of medical care requirements, wherein at least one of the plurality of information sources comprises the Internet and wherein the stream of data from the Internet comprises discussions, on at least one social media feed, by individuals related to a medical condition, wherein the receiving comprises mining the at least one social media feed, identifying symptoms within the at least one social media feed by parsing information mined from the at least one social media feed utilizing at least one natural language processing technique, and categorizing the symptoms as being related to the medical condition by accessing a database including information related to medical conditions and correlating the symptoms with the medical condition using the database;

determining, by analyzing a volume of information comprising the stream of data and at least one other stream of data, an influx of unpredicted medical patients for a predetermined facility within a healthcare enterprise system and having the medical condition, the determining being performed via sensing a trend in Internet context and related to the medical condition by identifying an increase in discussions of the medical condition and correlating the discussions to the predetermined facility that will experience the influx by filtering the stream of data based upon a geographic region associated with individuals corresponding to the discussions, wherein the determining comprises identifying a type of resource needed to treat the medical condition of at least a portion of the unpredicted medical patients by predicting, by analyzing the volume of information, a severity level of the medical condition of at least a portion of the unpredicted medical patients;

receiving, from the healthcare enterprise system, a notification, generated responsive to determining the predetermined facility will experience the influx of unpredicted medical patients, indicating a need for at least one medical resource during a predetermined time frame corresponding to an expected time frame of the influx of the unpredicted medical patients at the predetermined facility within the healthcare enterprise system, wherein the at least one medical resource corresponds to at least the type of resource needed to treat at least a portion of the unpredicted medical patients;

determining that the indicated need is unavailable during at least one of: the predetermined time frame and the predetermined facility by comparing the indicated need for the at least one medical resource during the predetermined time frame to an availability of the indicated need during the predetermined time frame;

identifying, based upon the indicated need being unavailable, at least one action to be performed to supply the at least one medical resource, wherein the at least one medical resource is needed during the predetermined time frame and identified based upon the influx of unpredicted medical patients, wherein the at least one action comprises finding a patient ready to be stepped down in care who is currently utilizing the at least one medical resource identified as the indicated need; and performing the at least one action to acquire the at least one medical resource not currently available during the predetermined time frame at the predetermined facility within the healthcare enterprise system via decompressing the healthcare enterprise system, thereby increasing availability of the at least one medical resource, wherein the at least one medical resource is based on at least one of: a severity of injury from the influx and a symptom from the influx, wherein the decompressing comprises rerouting patients scheduled to arrive at the predetermined facility to a facility other than the predetermined facility.

2. The method of claim 1, wherein the at least one medical resource comprises a bed in a facility downstream from an emergency department of the healthcare enterprise.

3. The method of claim 2, wherein the identifying at least one action comprises identifying at least one bed included in the facility that can be made available.

4. The method of claim 3, wherein the performing an action comprises rescheduling discharge times for the at least one bed included in the facility to occur prior to the predetermined time frame.

5. The method of claim 3, wherein the performing an action comprises scheduling environmental services to clean the at least one bed prior to the predetermined time frame.

6. The method of claim 1, wherein the at least one medical resource comprises at least one staff member.

7. The method of claim 6, wherein the identifying an action comprises accessing a staff scheduling system and identifying, within the staff scheduling system, a proposed scheduled for at the least one staff member.

8. The method of claim 7, wherein the performing an action comprises rescheduling the at least one staff member to be available during the predetermined time frame.

9. The method of claim 1, wherein the at least one medical resource comprises at least one medical procedure object.

10. The method of claim 9, wherein the identifying at least one action comprises identifying a current location of the at least one medical procedure object that is different from the predetermined facility and wherein the performing an action comprises providing instructions to transfer the at least one medical procedure object to the predetermined facility.

11. An information handling device, comprising:
a processor;
at least one sensor operatively coupled to the processor;
a memory device that stores instructions executable by the processor to:
receive, from at least one of a plurality of information sources, a stream of data relating to a set of predictive factors of medical care requirements, wherein at least one of the plurality of information sources comprises the Internet and wherein the stream of data from the Internet comprises discussions, on at least one social media feed, by individuals related to a medical condition, wherein the receiving comprises mining the at least one social media feed, identifying symptoms within the at least one social media feed by parsing information mined from the at least one social media feed utilizing at least one natural language processing technique, and categorizing the symptoms as being related to the medical condition by accessing a database including information related to medical conditions and correlating the symptoms with the medical condition using the database;
determine, by analyzing a volume of information comprising the stream of data and at least one other stream of data, an influx of unpredicted medical patients for a predetermined facility within a healthcare enterprise system and having the medical condition, the determining being performed via sensing a trend in Internet context and related to the medical condition by identifying an increase in discussions of the medical condition and correlating the discussions to the predetermined facility that will experience the influx by filtering the stream of data based upon a geographic region associated with individuals corresponding to the discussions, wherein the determining comprises identifying a type of resource needed to treat the medical condition of at least a portion of the unpredicted medical patients by predicting, by analyzing the volume of information, a severity level of the medical condition of at least a portion of the unpredicted medical patients;
receive, from the healthcare enterprise system, a notification, generated responsive to determining the predetermined facility will experience the influx of unpredicted medical patients, indicating a need for at least one medical resource during a predetermined time frame corresponding to an expected time frame of the influx of the unpredicted medical patients at the predetermined facility within the healthcare enterprise system, wherein the at least one medical resource corresponds to at least the type of resource needed to treat at least a portion of the unpredicted medical patients;

determine that the indicated need is unavailable during at least one of: the predetermined time frame and the predetermined facility by comparing the indicated need for the at least one medical resource during the predetermined time frame to an availability of the indicated need during the predetermined time frame;

identify, based upon the indicated need being unavailable, at least one action to be performed to supply the at least one medical resource, wherein the at least one medical resource is needed during the predetermined time frame and identified based upon the influx of unpredicted medical patients, wherein the at least one action comprises finding a patient ready to be stepped down in care who is currently utilizing the at least one medical resource identified as the indicated need; and perform the at least one action to acquire the at least one medical resource not currently available during the predetermined time frame at the predetermined facility within the healthcare enterprise system via decompressing the healthcare enterprise system, thereby increasing availability of the at least one medical resource, wherein the at least one medical resource is based on at least one of: a severity of injury from the influx and a symptom from the influx, wherein the decompressing comprises rerouting patients scheduled to arrive at the predetermined facility to a facility other than the predetermined facility.

12. The information handling device of claim 1, wherein the at least one medical resource comprises a bed in a facility downstream from an emergency department of the healthcare enterprise.

13. The information handling device of claim 12, wherein the identifying at least one action comprises identifying at least one bed included in the facility that can be made available.

14. The information handling device of claim 13, wherein the performing an action comprises rescheduling discharge times for the at least one bed included in the facility to occur prior to the predetermined time frame.

15. The information handling device of claim 13, wherein the performing an action comprises scheduling environmental services to clean the at least one bed prior to the predetermined time frame.

16. The information handling device of claim 11, wherein the at least one medical resource comprises at least one staff member.

17. The information handling device of claim 16, wherein the identifying an action comprises accessing a staff scheduling system and identifying, within the staff scheduling system, a proposed scheduled for the at least one staff member and wherein the performing an action comprises rescheduling the at least one staff member to be available during the predetermined time frame.

18. The information handling device of claim 11, wherein the at least one medical resource comprises at least one medical procedure object.

19. The information handling device of claim 18, wherein the identifying at least one action comprises identifying a current location of the at least one medical procedure object that is different from the predetermined facility and wherein the performing an action comprises providing instructions to transfer the at least one medical procedure object to the predetermined facility.

20. A product, comprising:
a storage device that stores code, the code being executable by a processor and comprising:

code that receives, from at least one of a plurality of information sources, a stream of data relating to a set of predictive factors of medical care requirements, wherein at least one of the plurality of information sources comprises the Internet and wherein the stream of data from the Internet comprises discussions, on at least one social media feed, by individuals related to a medical condition, wherein the receiving comprises mining the at least one social media feed, identifying symptoms within the at least one social media feed by parsing information mined from the at least one social media feed utilizing at least one natural language processing technique, and categorizing the symptoms as being related to the medical condition by accessing a database including information related to medical conditions and correlating the symptoms with the medical condition using the database;

code that determines, by analyzing a volume of information comprising the stream of data and at least one other stream of data, an influx of unpredicted medical patients for a predetermined facility within a healthcare enterprise system and having the medical condition, the determining being performed via sensing a trend in Internet context and related to the medical condition by identifying an increase in discussions of the medical condition and correlating the discussions to the predetermined facility that will experience the influx by filtering the stream of data based upon a geographic region associated with individuals corresponding to the discussions, wherein the determining comprises identifying a type of resource needed to treat the medical condition of at least a portion of the unpredicted medical patients by predicting, by analyzing the volume of information, a severity level of the medical condition of at least a portion of the unpredicted medical patients;

code that receives, from the healthcare enterprise system, a notification, generated responsive to determining the predetermined facility will experience the influx of unpredicted medical patients, indicating a need for at least one medical resource during a predetermined time frame corresponding to an expected time frame of the influx of the unpredicted medical patients at the predetermined facility within the healthcare enterprise system, wherein the at least one medical resource corresponds to at least the type of resource needed to treat at least a portion of the unpredicted medical patients;

code that determines that the indicated need is unavailable during at least one of: the predetermined time frame and the predetermined facility by comparing the indicated need for the at least one medical resource during the predetermined time frame to an availability of the indicated need during the predetermined time frame;

code that identifies, based upon the indicated need being unavailable, at least one action to be performed to supply the at least one medical resource, wherein the at least one medical resource is needed during the predetermined time frame and identified based upon the influx of unpredicted medical patients, wherein the at least one action comprises finding a patient ready to be stepped down in care who is currently utilizing the at least one medical resource identified as the indicated need; and code that performs the at least one action to acquire the at least one medical resource not currently available during the predetermined time frame at the predetermined facility within the healthcare enterprise system via decompressing the healthcare enterprise system, thereby increasing availability of the at least one medical resource, wherein the at least one medical resource is based on at least one of: a severity of injury from the influx and a symptom from the influx, wherein the decompressing comprises rerouting patients scheduled to arrive at the predetermined facility to a facility other than the predetermined facility.

* * * * *